United States Patent [19]

Burnhill

[11] Patent Number: 4,564,362
[45] Date of Patent: Jan. 14, 1986

[54] VAGINAL DEVICE

[76] Inventor: Michael S. Burnhill, Rte. 24 R.D. 2, Mendham, N.J. 07945

[21] Appl. No.: 511,759

[22] Filed: Jul. 7, 1983

[51] Int. Cl.$^4$ .......................................... A61F 13/20
[52] U.S. Cl. .................................. 604/286; 604/369; 604/904; 604/55
[58] Field of Search .................. 604/286, 369, 904, 55

[56] References Cited

U.S. PATENT DOCUMENTS

| | | | |
|---|---|---|---|
| 2,319,481 | 5/1943 | Stillman et al. | 424/28 E X |
| 2,541,103 | 2/1951 | Sander | 424/318 |
| 2,759,931 | 8/1956 | Drake et al. | 548/230 |
| 2,774,709 | 12/1956 | Mayhew et al. | 424/170 |
| 2,902,484 | 9/1959 | Horclois | 544/44 |
| 2,927,110 | 3/1960 | Gever et al. | 544/137 X |
| 3,084,689 | 4/1963 | Dankwardt | 604/286 |
| 3,762,414 | 10/1973 | Burnhill | 604/369 |
| 4,393,871 | 7/1983 | Vorhauer et al. | 609/58 |

Primary Examiner—William H. Grieb
Attorney, Agent, or Firm—Evelyn M. Sommer

[57] ABSTRACT

A vaginal device adapted for use as a disposable female contraceptive or as a disposable article for controllably dispensing drugs is provided comprising an outermost layer of resilient, compressible open-celled polymeric foam. Affixed to the outermost foam layer is a non-porous film layer made of a liquid proof, soft elastomeric material. Affixed to the non-porous film layer is another layer of open-celled polymeric foam. The intermediate film layer provides a barrier between the two foam layers. The outermost and innermost foam layers are formed from foams differing basically in density and/or number of pores per inch, with the more dense or smaller pored foam constituting the outermost layer, the outermost layer being adapted to lie against the cervix of the uterus and block the upper vaginal vault.

14 Claims, 9 Drawing Figures

VAGINAL DEVICE

This invention relates to a vaginal device and more particularly relates to a vaginal sponge used as a barrier contraceptive, as a carrier for a contraceptive or as a carrier and dispenser for medicaments. Still more particularly the invention relates to a disposable female contraceptive.

It is abundantly clear that one of the most crucial problems of man is the expanding population. Already the large cities are experiencing a disconcerting modern symptom of being "people trapped." What is more, the Malthusian nightmare of population exceeding the food supply has become a reality. Major efforts have been directed to thwart this crisis. The development of the oral contraceptive—i.e., the "pill", has been hailed as one of the major discoveries of our age and more significant to the human race than the release of atomic energy or space flights.

Unfortunately, there are side effects and certain risks involved in the taking of oral contraceptives. From 15 to 35% of the women using the oral contraceptives experience undesirable side effects. Nausea, vomiting, breast fullness, mastalgia, headache, dizziness, depression, apathy, fatigue, pelvic pain and chloasma are the most frequent. Fluid retention and weight gain are also observed. Thrombophlebitis has been the cause of greatest concern to the profession, the FDA and the public. Instances of jaundice have been reported. There has been some indication that contraceptive therapy may increase the blood pressure in a segment of the patients.

There are other contraceptive products available. They vary in mode of application, time of application, nature of device, cost, adverse affects and reliability. For the purpose of this disclosure, there may be mentioned the diaphragm, the cervical cap, foams, jellies, suppositories and the vaginal sponge.

The diaphragm and cervical cap involve the intervention of a physician and are expensive and in the case of the cervical cap may produce discomfort, infection and other problems. The foams, jellies and suppositories do not require a physician, are inexpensive and have the disadvantages that they are unpleasant and/or messy to use and have reliabilities of 85% or less.

A vaginal sponge contraceptive has been disclosed in U.S. Pat. No. 3,762,414 issued in 1973 to the inventor named herein. This sponge is a compressible, smooth surfaced, plastic sponge in the form of a solid rectangle, cylinder, sphere or the like and as disclosed is divided into two or more sections by a plastic, latex or other rubber sheet or film. The dividing sheet or film prevents the flow of fluid from one section of the sponge to the other. The sponge is used for controlling the flow of seminal fluid (contraception) and for dispensing medicaments.

The use of the sponge as a contraceptive is enhanced by incorporating into the sponge a spermicidal agent as, for example, a copper salt. Still further, the sponge as described in the patent may be used as a carrier and dispenser for medicaments, for example, as are used to treat infections.

As disclosed in U.S. Pat. No. 3,762,414, the vaginal sponge is produced from polyurethane foam or other smooth surfaced plastic foam and is divided into at least two sections separated by a plastic latex or other nonporous fluid impervious film. The contraceptive action is provided by sponge-like absorption of sperm by the foam material and blockage of the passage of such sperm by the films used to separate the sponge sections. Contraception is enhanced by the use of a chemical contraceptive which is absorbed and released in a sponge-like controlled manner.

Recently a non-prescription sponge contraceptive has been disclosed (V.L.I. Corporation of Costa Mesa, Calif.) which is round in shape and which is adapted to release a chemical, nonoxynol-9 that inactivates sperm. The sponge as in the case of the device disclosed in U.S. Pat. No. 3,762,414 also blocks the cervix and also acts to trap and absorb semen. As described by the press, "in clinical trials, the sponge was found to be about 85% effective in preventing pregnancy." U.S. Pat. No. 4,393,871 has been issued to the VLI corporation for the aforesaid contraceptive sponge.

It is an object of the present invention to provide a multi-purpose vaginal device suitable for use in contraception and medicament application improved as compared to the state of the art with respect to consumer acceptance, efficacy and production feasibility.

A further object of the invention is to provide a multi-purpose vaginal device that completely prevents fluid flow from one of its ends to the other and yet is porous and absorbent.

Still a further object of the present invention is to provide a vaginal contraceptive device having an improved effectiveness in preventing pregnancy.

Yet a further object of the invention is to provide a vaginal device of the type described which may be economically mass produced and which may be simply packaged to facilitate storage and transportation thereof prior to use.

Another object of the invention is to provide a vaginal device of the type described for controllably dispensing drugs.

Still another object of the invention is to provide a vaginal device of the type described in which access is provided to the device for easy removal thereof.

These and further objects and advantages of the invention will be made clear or will become apparent during the course of the following description.

In accordance with the present invention a vaginal device is provided the outermost layer of which is an open-celled polymeric foam. Affixed to the outermost foam layer is a non-porous film layer made of a liquid proof, soft elastomeric material. Affixed to the non-porous film layer is another layer of open-celled polymeric foam. The intermediate film layer provides a barrier between the two foam layers. The outermost and innermost foam layers are formed from foams differing basically in density and/or number of pores per inch, with the more dense or smaller pored foam constituting the outermost layer, the outermost layer being adapted to lie against the cervix of the uterus.

The contraceptive action is provided by sponge-like absorption of sperm by the foam and blockage of the passage of such sperm by suitable selection of the foam and by the film used to separate the outermost and innermost sponge layers. The effectiveness of the device is enhanced by the introduction of a chemical contraceptive into at least one of the sponge layers, preferably during the manufacturing process from which it is absorbed and released in a sponge-like controlled manner.

When the device is used as an article for controllably dispensing drugs, it can be appreciated that the same or different drugs can be introduced into at least one of the sponge layers and that these may be adapted for rapid release or for release over a prolonged period of time.

In the drawings which form an integral part of the specification and are to be read in conjunction therewith, and in which like parts are designated by like numerals in the various views.

Figure 1:
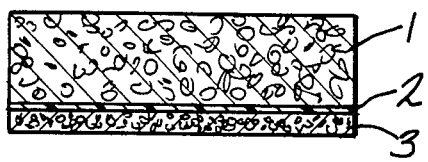
FIG. 1 is a sectional view of the vaginal device of the invention.

The device as constructed is cylindrical in shape and preferably forms a more or less circular unit having a diameter of about 2 3/5 and a depth of about ¾ inches. The invention is not limited to the foregoing dimensions, the same being illustrative only. Thus, the device may also be spherical or globular in shape or may take the form of a truncated cone. Its diameter may decrease somewhat but this aspect is limited as it is critical that the device form a barrier across the vaginal canal. Its depth may increase, however, to include dimensions of up to about 3 3/5 inches.

The outermost and innermost layers should have a thickness of from about ⅛ inch up to about 1¾ inch each. Preferably the outermost layer is about ⅝ inch thick and the innermost layer about ⅛ inch thick. Such thicknesses insure ready impermeability yet also provide flexibility.

The barrier film should have a thickness of about 0.5 to about 3 mils, preferably from 1 to 2 mils.

As noted hereinabove, the device in use must be positionable to close the cervical opening and for sealingly abutting the walls of the vaginal canal.

The foam must of course be biocompatible and is preferably a polyurethane foam. Any polyurethane foam which can be fabricated with the characteristics needed for the intended end use may be employed.

While the polyurethane foams are preferable, there are not presently any reasons why the polyester, polyether, polyethylene, crosslinked polyethylene and the like combination foams as for example polyester-polyurethane foams may not be used. The criteria for selection of course must include in addition to effectiveness, safety for their intended use.

Preferably, the foams are open cell, but it would appear that closed cell foams would work as well. The cell structure most preferably is open cell, 80–200 pores per inch. The density of the foam will vary as hereinafter described but can range from 1.5 to 3.0 lbs. per cu. ft. and even higher.

The tensile strength characteristics are somewhat important and should amount to about 30–39 psi. It can be appreciated that the foams involved are readily available and that there is no difficulty envisioned should there be a need to custom fabricate so as to produce the desired characteristics.

Most important, the sponge must be permeable, it must be capable of absorbing, retaining and then releasing a spermicide or medicament. At the same time, it must be a barrier for the microsized highly mobile sperm.

Foams marketed under the trade names Scott Industrial Foam, Scottfelt Foam, Pyrell and the like are particularly suitable for use in producing the device of the invention. Two foams are used in constructing the instant device with the foams being selected so as to provide layers of differing resiliency, stiffness and absorbency. The density and cell structure, particularly the pores per inch, determine the characteristics. As noted above the more dense or smaller pored foam is selected for forming the outermost layer.

The foam layers are separated one from the other by a barrier film. The film barrier can be made of natural rubber, synthetic rubber or latex material, or other elastomeric material. It is also possible to use as barrier layer certain of the laminated packaging materials, as for example a barrier coextruded layer comprised of a two or three layer combination of ethylene methylacrylate copolymer and polyester. It is contemplated that in place of the barrier film a glue layer may be used. As glue there may be used any suitable adhesive i.e., one which is pharmacologically acceptable and capable of forming an impervious layer. An example of such an adhesive layer is a polyolefin adhesive layer. Another adhesive which may be used is ethylene acrylic acid.

The layers of sponge are so arranged as to provide an outermost layer forming an expansion collar which aids in securing the device, holding the device in position, and which furthermore reinforces the barrier effect of the film and innermost sponge layer.

The use of a string or thread or woven fabric ribbon is contemplated for facilitating removal and/or withdrawal of the device.

The sponge (one or both layers) for contraceptive use may be impregnated with a spermicide, preferably during the manufacturing process, such as nonoxynol-9, which has long been recognized as safe and effective for this purpose. Other examples of spermicides which are suitable for use herein include nonylphenoxypolyethoxyethanol, methoxypolyoxyethyleneglycol 550 laurate, stearic acid, ricinoleic acid, p-diisobutylphenoxyethoxyethanol and the like.

Most important, the sponge may be used as means for dispensing medicaments as for example, anti-infection agents, anti-microbials, hormones, enzymes, psychotropic drugs, cardiac and blood pressure regulators, etc. This aspect of the invention is considered to be a very important one.

Illustrative of the suitable medicaments and the categories in which they fall are the following:

| Name | Category |
| --- | --- |
| aminophylline | smooth muscle relaxant |
| aspirin | analgesic |
| diethylstilbesterol | estrogen |
| iodochlorhydroxyquin | local anti-infective |
| carbasone | anti-trichomonal |
| furazolidone | antibacterial |
| nitrofuroxione | antiprotozoan |
| prochlorperazine | tranquilizer |
| trimethobenzamide | anti-emetic |

| Name | Category |
| --- | --- |
| hydrochloride and benzocaine | |

Other medicaments which can be mentioned are barbital, chloralhydrate, cocaine hydrochloride, digitalis leaf, phenobarbital, procaine, sulfanilamide, sulfathiazole, sulfonal and the like.

The medicaments can be introduced into the sponge layers during the manufacturing process, singly or in combination, into one or both of the layers, in a rapid release, or relatively long duration or prolonged release form.

The vaginal sponge of the invention can be fabricated by any of the conventional foam techniques. The incorporation of the film between the two foam layers is known, as are the techniques for making the foams. Any of the known methods of molding, extrusion, stamping, etc., may be used singly or in combination to make the device. To the same end, the conventional techniques for loading the sponge with spermicide and/or medicament for storage and controlled release thereof may be employed.

Referring to FIG. 1, an outermost layer of open cell polyurethane foam 1 having about 150 psi and having a thickness of about ⅜ inch is affixed to a latex film 2 having a thickness of about 1.5 mils. The innermost layer is an open cell polyurethane foam having about 100 psi and having a thickness of about ⅛ inch. The device is a cylindrical construction having a diameter of about 2 3/5 inches and a thickness just exceeding ¾ inches.

Figure 2:
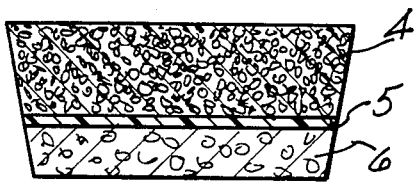
FIG. 2 is a sectional view of an alternate form of the vaginal device of the invention.

As illustrated in FIG. 2, the device is of a truncated cone construction composed of two different foams, a more dense foam 4 i.e., Scottfelt foam having a density of about 3 lbs/cu. ft. separated by a latex film barrier layer 5 from a less dense foam layer 6 i.e., Scott Industrial Foam (fine porosity) having a density of about 1.75 lbs. per cu. ft. The total thickness of the construction is about 1 inch. The outermost layer of more dense foam is about twice as thick as the innermost layer. The latex film is approximately 2.0 mils in thickness.

Figure 3:
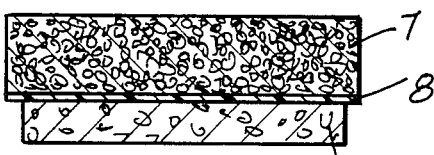
FIG. 3 is a sectional view of yet another form of the vaginal device of the invention.

In the construction shown in FIG. 3, a sponge device is provided in which the edge of the more dense layer of foam 7 protrudes slightly beyond the edge of the less dense sponge layer 9. The barrier film layer 8 extends over the entire inner edge of the layer 7. In this instance layer 7 is made of Pyrell (polyester) has a density of about 3.0 lbs/cu. ft. and layer 9 is made of a less dense Pyrell i.e., having a density of 2.5 lbs./cu. ft.

As illustrated, this edge composed of the more dense foam sponge but still resilient sponge is partially compressed during the act of insertion. It is the outward pressure of this sponge layer that produces a gentle but effectual grasping and retention of the device contributing in no small measure to its increased effectiveness.

Figure 4:
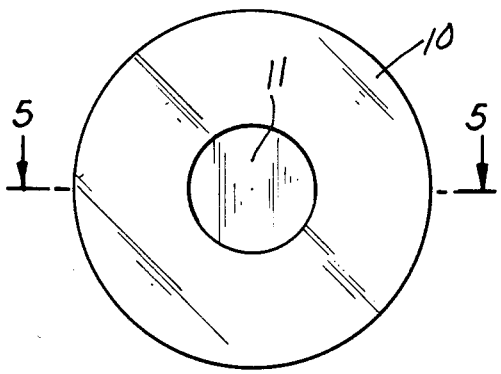
FIG. 4 is a plan view of still another form of the vaginal device of the invention.
Figure 5:
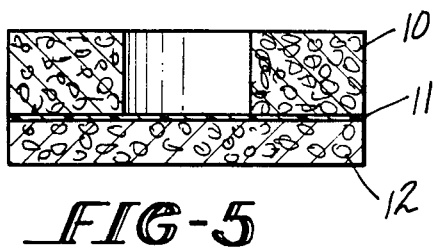
FIG. 5 is a sectional view taken along the line 5—5 in FIG. 4.

The embodiment shown in FIGS. 4 and 5 is a particularly preferred vaginal contraceptive construction. In this instance the topmost or outermost layer 10 is constructed in the form of an "O" ring, the barrier layer 11 being exposed at the center portion thereof. However, the barrier layer and the innermost layer are continuous. The result of this construction is that while the barrier across the vaginal canal is retained the device is particularly well adapted to lie against the cervix of the uterus and the edges of the outermost layer 10 being adapted to block the vaginal fornices.

While the device constituting my invention has been described as being more or less circular in shape, other shapes, i.e., elliptical, pear and the like, are contemplated.

In the same manner, while the device has been disclosed as consisting of two (2) layers of sponge separated by a layer of impervious film, it is of course possible to have additional layers of sponge. However, at least one layer of impervious film must be present and disposed between two layers of sponge, i.e., only one layer of impervious film is required, regardless of how many foam layers are present.

Figure 8:
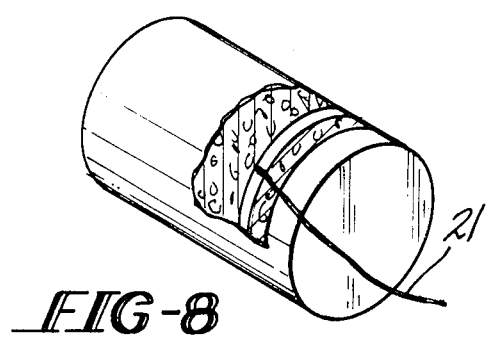
FIG. 8 is a perspective view showing another embodiment of the invention directed toward facilitating removal of the device.

In FIG. 8, the device as shown is composed of two layers, with a total thickness of about 2 inches. In this embodiment for facilitating removal, a withdrawal string 21 made of cotton or nylon thread is provided. In place of the string a woven or non-woven tape may be substituted.

Figure 6:
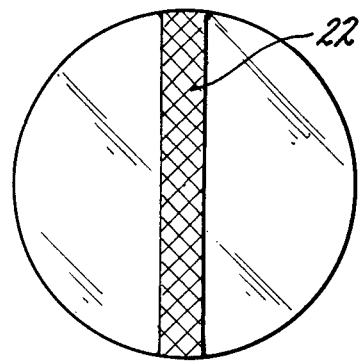
FIG. 6 is a plan view showing a strip attachment for facilitating removal of device after use.
Figure 7:
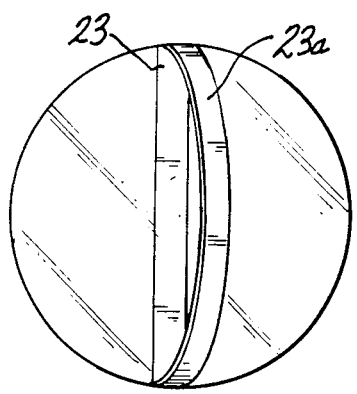
FIG. 7 is a plan view showing yet another type of attachment for use in removal of the device.

FIGS. 6 and 7 illustrate alternate means for facilitating removal of the device. In FIG. 6 a strap 22 made of a woven natural non-irritating material is provided, while in FIG. 7 a flap 23 of a non-irritating material is provided. The flap is provided with a free end 23a which can be grasped for withdrawal of the device.

Figure 9:
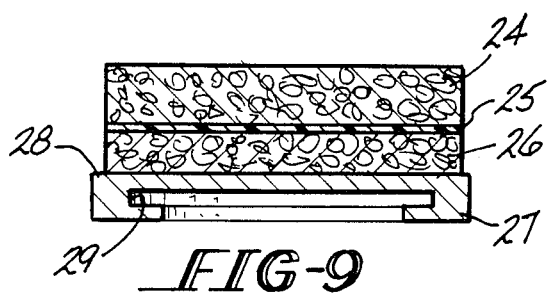
FIG. 9 is a sectional view of a further embodiment of the invention directed toward facilitating removal of the device.

As illustrated in FIG. 9, in addition to the foam and film barrier layers 24, 25 and 26, a flange like layer of dense foam 27 which can be open or closed cell such as a layer of Volara (cross-linked polyethylene foam) having a density of about 5 lbs per cu. ft. is affixed to the innermost layer 26. The layer 27 is fabricated to provide a finger gripping area 28 and/or 29. The flange layer in this instance is about ¼ inch in thickness. It can be appreciated that while a continuous flange is shown in the drawing the flange section can be provided as a one-sided structure.

As a further embodiment, it is contemplated that a layer of suitable adhesive (pharmacologically acceptable and forming an impervious barrier layer) may be substituted for the elastomeric film layer in any of the above embodiments.

The following examples are given in order to more fully illustrate the invention and are not to be construed as limitative thereof:

EXAMPLE 1

During the process of manufacture of a device as shown in FIG. 3 there is incorporated into both foam layers 4 and 6 the spermicide nonoxynol-9 (poly(ethyleneglycol) p-nonyl phenylether). This compound is known (U.S. Pat. No. 2,541,103) and its preparation is disclosed in U.S. Pat. No. 2,774,709. The device is eminently suitable as a disposable female contraceptive.

EXAMPLE 2

During the process of manufacture, there is incorporated into a device as shown in FIG. 4, prochlorperazine (2-chloro-10-[3-(4-methyl-1-piperazinyl)-propyl]-1OH-phenothiazine. This compound is a known tranquilizer. Its preparation is described in U.S. Pat. No. 2,902,484. The device is eminently suitable for controllably dispensing this medicament and is particularly useful where difficulty in administering such medicament orally is encountered.

EXAMPLE 3

In place of prochlorperazine, a combination of furazoli-done (3[[5-nitro-2-furanyl)methylene]-amino]-2-oxazolidinone) (U.S. Pat. No. 2,759,931 and 2,927,110) and nitrofuroxime (5-nitro-2-furancarbox-aldehyde oxime) (U.S. Pat. No. 2,319,481), both known anti-bacterials and antiprotozoan compounds are incorporated into the device described in Example 2 and resulted in a markedly effective anti-effective antibacterial and antiprotozoal agent. The same desirable results were realized when the foregoing combination was replaced by metronitrazole (Searle) having trichomonical and anti-bacterial effectiveness.

As described above, the medicaments and spermicide are dispersed from the surface of the device into the surrounding medium. As the medicament or spermicide is removed from the surface further amounts migrate to the surface until the supply of spermicide or medicament is exhausted.

It is well within the skill of the art to control the rate of dispensing so as to provide the active agents as indicated for conventional and/or prolonged release forms.

It is also believed that the artisan and the user are well aware of how the device is to be inserted and removed and that accordingly the details therefore need not be expressly set forth.

What is claimed is:

1. A vaginal device consisting essentially of an outermost layer of resilient compressible open-celled polymeric foam, a non-pororous barrier film layer formed of a liquid proof, soft elastomeric material affixed to said outermost foam layer and a second layer of open-celled polymeric foam affixed to the opposite surface of said non-porous film layer, said outermost and innermost foam layers differing in density and/or numbers of pores per inch with the more dense or smaller pored foam layer constituting the outermost layer, said outermost layer forming an expansion collar and being adapted to lie against the cervix of the uterus, where it aids in holding and securing the device in position and additionally reinforces the barrier effect of the film and innermost foam layer.

2. A vaginal device according to claim 1, being cylindrical in shape and having a diameter of about 1½ to about 3 3/5 inches and a depth of about ½14 2½ inches.

3. A vaginal device according to claim 1 being circular in shape and having a diameter of about 2 3/5 inches and a depth of about ¾ inches.

4. A vaginal device according to claim 2 wherein said innermost and outermost layers each have a thickness of from about ⅛ inch to about 1¾ inches.

5. A vaginal device according to claim 3 wherein said outermost layer is about ⅝ inch thick and said innermost layer is about ⅛ inch thick.

6. A vaginal device according to claim 1 wherein said intermediate film layer has a thickness of about 0.5 to about 3 mils.

7. A vaginal device according to claim 1 wherein said polymeric foams are formed from polyurethane, polyester, polyether, polyethylene or combinations thereof.

8. A vaginal device according to claim 1, wherein said foams are open-celled foams.

9. A vaginal device according to claim 8, wherein said foams have 80–200 pores per square inch.

10. A vaginal device according to claim 1, wherein said non-porous film layer is made of natural rubber, synthetic rubber or a latex material.

11. A vaginal device according to claim 1, adapted for use as a female disposable contraceptive wherein at least one of said polymeric foam layers has incorporated therein a contraceptive agent.

12. A vaginal device according to claim 11, wherein said contraceptive agent is nonoxynol-9.

13. A vaginal device according to claim 1, adapted for use for controllably dispensing medicaments wherein at least one of said polymeric foam layers has incorporated therein at least one member of the group of anti-infection agents, antimicrobials, hormones, enzymes, psychotropic drugs, cardiac drugs, analgesics, blood pressure regulators, smooth muscle relaxants and anti-emetics.

14. A vaginal device according to claim 1, wherein said device includes means for facilitating its removal after use.

* * * * *